United States Patent
Camussi et al.

(10) Patent No.: US 9,499,796 B2
(45) Date of Patent: Nov. 22, 2016

(54) ISOLATED MULTIPOTENT MESENCHYMAL STEM CELL FROM HUMAN ADULT GLOMERULI (HGL-MSC), A METHOD OF PREPARING THEREOF AND USES THEREOF IN THE REGENERATIVE MEDICINE OF THE KIDNEY

(75) Inventors: Giovanni Camussi, Turin (IT); Stefania Bruno, Turin (IT); Benedetta Bussolati, Turin (IT)

(73) Assignee: FRESENIUS MEDICAL CARE DEUTSCHLAND GMBH, Bad Homberg (DE)

( * ) Notice: Subject to any disclaimer, the term of this patent is extended or adjusted under 35 U.S.C. 154(b) by 407 days.

(21) Appl. No.: 13/127,589

(22) PCT Filed: Nov. 2, 2009

(86) PCT No.: PCT/EP2009/064468
§ 371 (c)(1),
(2), (4) Date: Jun. 28, 2011

(87) PCT Pub. No.: WO2010/052192
PCT Pub. Date: May 14, 2010

(65) Prior Publication Data
US 2011/0256111 A1   Oct. 20, 2011

(30) Foreign Application Priority Data
Nov. 4, 2008  (EP) .................................. 08425708

(51) Int. Cl.
C12N 5/07     (2010.01)
C12N 5/071    (2010.01)
C12N 5/0775   (2010.01)

(52) U.S. Cl.
CPC .......... *C12N 5/0687* (2013.01); *C12N 5/0668* (2013.01)

(58) Field of Classification Search
CPC ............... C12N 5/0687; C12N 5/0668; C12N 5/071; C12N 5/0775
See application file for complete search history.

(56) References Cited

U.S. PATENT DOCUMENTS

2008/0112939 A1*  5/2008  Colter et al. ............... 424/93.21

FOREIGN PATENT DOCUMENTS

WO    WO 2007/125088    11/2007
WO    WO 2008/045498     4/2008

OTHER PUBLICATIONS

Schallmoser et al., Blood, vol. 108, No. 11, Part 1, pp. 1042A, Abstract 3649, 2006.*
Bussolati et al. Identification of a Tumor-Initiating Stem Cell Population in Human Renal Carcinomas; The FASEB Journal, vol. 22, No. 10 (2008) pp. 3696-3705.*
K. E. Schwab et al, "Co-expression of two perivascular cell markers isolates mesenchymal stem-like cells from human endometrium"; Human Reproduction, vol. 22, No. 11, pp. 2903-2911, 2007.
L. Da Silva Meirelles et al, "Mesenchymal stem cells reside in virtually all post-natal organs and tissues"; Journal Cell Science 119, pp. 2204-2213, 2006.
S. Bruno et al, "Isolation and Characterization of Resident Mesenchymal Stem Cells in Human Glomeruli", Stem Cells and Devel., vol. 18, No. 6, 2009, pp. 867-879.
C. Sagrinati et al, "Isolation and Characterization of Multipotent Progentior Cells from the Bowman's Capsule of Adult Human Kidneys"; Amer. Soc. Of Nephrology, 2006, pp. 2443-2456.
K. Le Blanc et al; HLA expression of immunologic properties of differentiated and undifferentiated mesenchymal stem cells; Int. Soc. For Experimental Hematology 31; 2003; pp. 890-896.
U. Noth et al; "Multilineage mesenchymal differentiation potential of human trabecular bone-derived cells"; J. Orthopaedic Research 20; 2002, pp. 1060-1069.
J. Perry et al; "Type IV Collagen Induces Podocytic Features in Bone Marrow Stromal Stem Cells In Vitro"; Amerc. Soc. Of Nephrology 17; 2006; pp. 66-76.
A. Maeshima et al; "Identification of Renal Progentitor-Like Tubular Cells that Participate in the Regeneration Processes of the Kidney"; J. Am Soc Nephrol 14; 2003, pp. 3138-3146.
J. Oliver et al; "Metanephric mesenchyme contains embryonic renal stem cells"; Am J. Physiol Renal Physiol 283; 2002; pp. F799-F809.
M. Pittenger et al; "Multilineage Potential of Adult Human Mesenchymal Stem Cells"; Science 284; 1999; 143-147.
E. Mayer et al; "Neural progenitor cells from postmortem adult human retina"; Br J Ophthalmol 2005; 89; pp. 102-106.
J. Oliver et al; "The renal papilla is a nich for adult kidney stem cells"; Journal of Clinical Investigation 114, No. 6; 2004; pp. 795-803.
G. Challen et al; "Identifying the Molecular Phenotype of Renal Progenitor Cells"; J Am Soc Nephrol 15; 2004; pp. 2344-2357.
G. Chamberlain; "Concise Review: Mesenchymal Stem Cells: Their Phenotype, Differentiation Capacity, Immunological Features, and Potential for Homing", Stem Cells 2007; vol. 25; pp. 2739-2749.
F. Collino et al; "Preeclamptic sera induce nephrin shedding from podocytes through endothelin-1 release by endothelial glomerular cells"; Am J Physiol Renal Physiol 294; 2008; F1185-F1194.
B. Dekel; "Isolation and Characteriation of Nontubular Sca-1+Lin- Multipotent Stem/Progenitor Cells from Adult Mouse Kidney"; J Am Soc Nephrol 17; 2006; pp. 3300-3314.

(Continued)

*Primary Examiner* — Scott Long
*Assistant Examiner* — Paul Martin
(74) *Attorney, Agent, or Firm* — Jacobson Holman, PLLC.

(57) ABSTRACT

The invention relates to an isolated multipotent glomerular mesenchymal stem cell derived from adult human kidney (hGL-MSC), which is characterized by the marker profile CD133$^-$, CD146$^+$, CD34$^-$ and CD105$^+$. A method of preparing the hGL-MSC of the invention form decapsulated glomeruli is also disclosed, as well as the uses of the hGL-MSC of the invention in the regenerative treatment of the kidney, particularly for the treatment of injuries or diseases affecting renal glomeruli.

16 Claims, 4 Drawing Sheets

(56) References Cited

OTHER PUBLICATIONS

M. Di Nicola et al; "Human bone marrow stromal cells suppress T-lymphocyte proliferation induced by cellular or nonspecific mitogenic stimuli"; Blood 2002 99; pp. 3838-3843.
V. El-Helou et al; "Resident Nestin + Neural-Like Cells and Fibers Are Detected in Normal and Damaged Rat Myocardium"; Hypertension 2005; vol. 46; pp. 1219-1225.
S. Gronthos et al; "Postnatal human dental pulp stem cells (DPSCs) in vitro and in vivo"; PNAS; 2000; vol. 97; 13625-13630.
S. Aggarwal et al; "Human mesenchymal stem cells modulate allogeneic immune cell responses"; Blood; 2005; pp. 1815-1822.
B. Bussolati et al; "Isolation of Renal Progenitor Cells from Adult Human Kidney"; American Journal of Pathology, vol. 166; 2005; pp. 545-555.
Cavaleri et al; "Nanog: A New Recruit to the Embryonic Stem Cell Orchestra"; Cell, vol. 113; 2003; pp. 551-552.
M. Tai et al; "Oct4 expression in adult human stem cells: evidence in support of the stem cell theory of carcinogenesis"; Carcinogenesiss vol. 26 No. 2; 2005; pp. 495-502.
Y. Sugiyama-Nakagiri; "Expression of RNA-Binding Protein Musashi in Hair Follicle Development and Hair Cycle Progression"; American Journal of Pathology, vol. 168, No. 1; 2006; pp. 80-92.
D. Prockop; "Marrow Stromal Cells as Stem Cells for Nonhematopoietic Tissues"; Science 276; 1997; pp. 71-74.
S. Rafii et al; "Vascular and Haematopoietic Stem Cells: Novel Targets for Anti-Angiogenesis Therapy?"; Div. Of Hematology-Oncology, Cornell Univ., Nature Publishing Group, vol. 2; 2002; pp. 826-835.
J. Ross et al; "Cytokine-induced differentiation of multipotent adult progenitor cells into funcctional smooth muscle cells"; J Clinical Investigation vol. 116. No. 12; 2006; pp. 3139-3149.
F. Sabatini et al; "Human bronchial fibroblasts exhibit a mesenchymal stem cell phenotype and multilineage differentiating potentialities"; Laboratory Investigation; 2005; pp. 962-971.
A. Suzuki et al; "Platelet-derived growth factor plays a critical role to convert bone marrow cells into glomerular mesangial-like cells"; Kidney International, vol. 65; 2004; pp. 15-24.

M. Vaughan et al; "ATRA induces podocyte differentiation and alters nephrin and podocin expression in vitro and in vivo"; Kidney International, vol. 68; 2005; pp. 133-144.
H. Young et al; "Human Reserve Pluripotent Mesenchymal Stem Cells Are Present in the Connective Tissues of Skeletal Muscle and Dermis Derived From Fetal, Adult, and Geriatric Donors"; The Anatomical Record 264; 2001;; pp. 51-62.
N. Zvaifler et al; "Mesenchymal precursor cells in the blood of normal individuals"; Arthritis Res 2000; pp. 477-488.
S. Gupta et al; "Isolation and Characterization of Kidney-Derived Stem Cells"; J Am Soc Nepphrol 17; 2006; pp. 3028-3040.
S. Hatano et al; "Pluripotential competence of cells associated with Nanog activity"; Mechanisms of Development 122; 2005; pp. 67-79.
M. Herrera et al; "Isolation and Characterization of a Stem Cell Population from Adult Human Liver"; Stem Cells; 2006; pp. 2840-2850.
M. Hoogdiujn et al; "Human Heart, Spleen, and Perirenal Fat-Derived Mesenchymal Stem Cells Have Immunomodulatory Capacties"; Stem Cells and Development 16; 2007; pp. 597-604.
S. Kitamura et al; "Establishment and characterization of renal progenitor like cells from S3 segment of nephron in rat adult kidney"; The FASEB Journal, vol. 19; 2005; pp. 1789-1797.
V. Lama et al; "Evidence for tissue-resident mesenchymal stem cells in human adult lung from studies of transplanted allografts"; The Journal of Clinical Investigation vol. 117, No. 4; 2007; pp. 989-996.
E. Lazzeri et al; "Regenerative Potential of Embryonic Renal Multipotent Progenitors in Acute Renal Failure"; J Am Soc Nephrol 18; 2007; pp. 3128-3138.
C. De Bari et al; "Multipotent Mesenchymal Stem Cells From Adult Human Synovial Membrane"; Arthritis & Rheumatism vol. 44; 2001; pp. 1928-1942.
P. Zuk et al; "Multilineage Cells from Human Adipose Tissue: Implications for Cell-Based Therapies"; Tissue Engineering vol. 7, No. 2; 2001; pp. 211-228.
C. Pollen et al; "Identification of a putative intestinal stem cell and early lineage marker; musashi-1"; Differentiation 71; 2003; pp. 28-41.
G. Challen et al; "Kidney Side Population Reveals Multilineage Potential and Renal Functional Capacity but also Cellular Heterogeneity"; J Am Soc Nephrol 17; 2006; pp. 1896-1912.

\* cited by examiner

ISOLATED MULTIPOTENT MESENCHYMAL STEM CELL FROM HUMAN ADULT GLOMERULI (HGL-MSC), A METHOD OF PREPARING THEREOF AND USES THEREOF IN THE REGENERATIVE MEDICINE OF THE KIDNEY

This is a national stage of PCT/EP09/064468 filed Nov. 2, 2009 and published in English, which claims the priority of European number 08425708.8 filed Nov. 4, 2008, hereby incorporated by reference.

TECHNICAL FIELD

The present invention relates to a multipotent human mesenchymal stem cell which is derived from decapsulated glomeruli of adult human kidney and shows the ability to differentiate into a variety of cell types, particularly glomerular cell types, and which at the same time is characterised by remarkable self-renewal and clonogenic abilities. Furthermore, the invention relates to a method of preparing the multipotent human mesenchymal stem cell of the invention and to the use of such stem cell in regenerative medicine, particularly in the therapeutic treatment of renal injury and disease.

PRIOR ART

Stem cell transplantation is known to possess the potential for repairing and regenerating damaged or injured tissues and organs. Consequently, intensive studies have been carried out in recent years in order to identify and isolate new multipotent stem cells from both human and animal origin, as well as to investigate the effectiveness of stem cells in clinical applications, especially regenerative medicine.

For example, Oliver et al. [3] identified slow cycling stem cells in the papilla of adult rodent kidneys, based on BrdU retention. Using the same approach, Maeshima et al. [4] identified BrdU labelled cells in the renal tubules of adult rats and showed the potential of such stem cells to generate proximal tubules and collecting duct cells or fibroblasts when transplanted into the metanephric kidney. Kitamura et al. established and characterized a distinct population of renal progenitor cells from the S3 segment of the nephron in the rat adult kidney [37]. These cells were shown to possess self-renewal abilities and to express renal embryonic markers such as Pax2, Wtn4 and Wtn1. Based on the ability to extrude Hoechst dye, a so called "side population" with multipotent potential was identified in mouse embryonic and adult kidney [38]. Recently, Gupta et al. demonstrated the presence in the adult rat kidney of a renal resident population of multipotent renal progenitor cells expressing embryonic stem cell markers such as Oct-4 and Pax-2 [5]. However, in view of their animal origin, these multipotent renal stem cells cannot be used in clinical applications relating to regeneration of human tissues or organs.

Identification of a population of multipotent CD133[+] CD24[+] stem cells from embryonic human kidneys has been disclosed in [39]. However, these embryonic stem cells do not represent an optimal solution to the problem of providing human stem cells for use in regenerative medicine, particularly in view of the ethical concerns associated with embryonic stem cell lines and their preparation form human embryos.

In the human adult kidney the present inventors previously disclosed a resident population of CD133[+] progenitors/stem cells [1]. The CD133[+] cells were found as rare cells in the interstitium in proximity of proximal tubules and glomeruli or within tubules, and they were shown to undergo renal epithelial and endothelial differentiation both in vitro and in vivo. Recently, Sagrinati et al. isolated and characterized a population of multipotent CD133[+]CD24[+] cells from the Bowman's capsule of adult kidneys [2]. However, the CD133[+] progenitors/stem cells identified in the human kidney are characterized by poor self-renewal abilities. Furthermore, such stem cells have not been shown to posses the ability to differentiate into the various cell types found in the renal glomerulus, that is to say podocytes, endothelial and mesangial cells.

Schwab et al., Human Reproduction (Oxford), vol. 22, no. 11, November 2007, pages 2903-2911, disclose endometrial CD146+ PDGF-Rβ+ CD34+ mesenchimal stem cells showing the classical differentiation abilities of MSCs, i.e. differentiation into adipogenic, osteogenic, chondrogenic and myogenic lineages. This paper is silent as to further differentiation abilities. However, the endometrial origin of these cells strongly points against their having the ability to give rise to glomerular cell types such as podocytes, mesangial and endothelial cells.

WO 2008/045498 discloses a CD34+ CD133− CD105− kidney-derived cell population which is capable of differentiating into adipocytes and osteoblasts. However, no differentiation into glomerular cell types is disclosed.

Mesenchymal stem cells (MSCs) are characterized by their ability to differentiate into different cell lines of mesenchymal origin [7]. The major reservoir of mesenchymal stem cells is the bone marrow (BM) [8]. However, recent data obtained in a murine model have demonstrated that the MSC compartment is more widely distributed. In fact MSCs have been detected virtually in all murine adult tissue (spleen, muscle, kidney, lung, liver, brain, thymus) in association with the vessel walls [6]. In humans, MSCs have been isolated from circulating blood and from several tissues such as synovium, adipose tissue, trabecular bone, dental pulp, dermis and lung [9-16]. However, the presence of MSCs in human glomeruli has been not investigated so far.

SUMMARY OF THE INVENTION

In the light of the foregoing, there is a need for mesenchymal stem cells derived from human adult kidney capable of differentiating into the various cell types found in the renal glomerulus and capable of self-renewal, so as to be successfully applicable in the regenerative medicine of the kidney, particularly as a medicament for the therapeutic treatment of injuries and/or diseases affecting the human kidney, more particularly injuries and/or diseases affecting renal glomeruli.

These and other objects are achieved by the isolated multipotent human mesenchymal stem cell identified and isolated by the present inventors in the decapsulated glomeruli of the human adult kidney.

Thus, a first aspect of the present invention is an isolated multipotent glomerular mesenchymal stem cell derived from adult human kidney (hGL-MSC), characterised in that it is CD133(negative), CD146(positive), CD34(negative) and CD105(positive).

The isolated multipotent glomerular mesenchymal stem cell derived from adult human kidney (hGL-MSC) is advantageously capable of differentiating into glomerular cell-types, i.e. podocytes, mesangial and endothelial cells.

In a preferred embodiment of the invention, the hGL-MSC is further characterised in that it is CD24(positive) and Pax-2(positive).

In a further preferred embodiment of the invention, the hGL-MSC is further characterised in that it is α-SMA (negative) and Oct-4(negative).

Another aspect of the invention is a method of preparing the hGL-MSC of the invention, comprising the following steps:

culturing decapsulated glomeruli from human adult kidney in an expansion culture medium comprising a serum-containing animal cell culture medium buffered at physiological pH and in the absence of specific growth factors, thereby obtaining a mixed population of cells outgrowing from the cultured decapsulated glomeruli, said mixed population of cells containing both spindle-shaped CD133(negative), CD146(positive) cells and CD133(positive), CD146(positive) cells; and isolating the spindle-shaped CD133(negative), CD146 (positive) cells from the mixed population, said spindle-shaped cells CD133(negative), CD146(positive) representing the hGL-MSCs of the invention.

According to a preferred embodiment, the expansion culture medium is buffered at a pH comprised within the range of 6.8 to 7.4, more preferably within the range of 7.2 to 7.4. Any buffering agent capable of maintaining the pH within the physiological range may be used, such as for example Hepes, PBS or the like.

In another preferred embodiment, the spindle-shaped CD133(negative), CD146(positive) cells, which represent the hGL-MSCs of the invention, are isolated from at least the $3^{rd}$ passage of cell culture or from a subsequent passage of cell culture, such as for example from the $4^{th}$ passage, the $5^{th}$ passage, the $6^{th}$ passage, etc. This embodiment is based on the fact that the spindle-shaped CD133(negative), CD146 (positive) cells are the only cell type in the mixed population which was found to survive after the $3^{rd}$ passage of cell culture under the above-mentioned culture conditions.

In an embodiment of the invention, the spindle-shaped CD133(negative), CD146(positive) cells are isolated from the mixed population by a cell sorting method such as FACS. Alternatively, they can be isolated based on their spindle-shaped morphology.

The hGL-MSCs of the invention are advantageously characterised by remarkable self-renewal and clonogenic abilities and by the ability to differentiate into a number of glomerular cell types, including but not limited to endothelial cells, mesangial cells and podocytes. These features make the hGL-MSCs of the invention particularly suitable for use in kidney regeneration.

Thus, a further aspect of the invention is the use of the isolated human glomerular mesenchimal stem cell of the invention (hGL-MSC) as a medicament for the therapeutic treatment of kidney injuries or diseases, particularly injuries or disease affecting the renal glomerulus.

A further aspect of the invention is a pharmaceutical composition comprising the isolated human glomerular mesenchimal stem cell of the invention (hGL-MSC) and a pharmaceutically acceptable carrier, diluent and/or vehicle. A pharmaceutical composition comprising the human glomerular mesenchimal stem cell of the invention (hGL-MSC) is particularly suitable for the treatment of kidney injuries or diseases, particularly injuries or disease affecting the renal glomerulus.

DESCRIPTION OF THE DRAWINGS

Further advantages and features of the invention will be apparent from the following detailed description with reference to the appended drawings, wherein:

FIG. 3 shows the immunomodulatory properties of hGL-MSCs and their cloning efficiency. A) Representative FACS analyses showing that hGL-MSCs are negative for class II antigens and the adhesion molecule CD154 as well as the co-stimulatory molecules CD80, CD86 and CD40 (dark line). The dotted lines are the isotypic controls. B) The addition of bone marrow mesenchymal stem cells (BM-MSCs) or human glomerular mesenchymal stem cells (hGL-MSCs) of the invention inhibits PHA-induced PBMC proliferation. PBMCs ($5 \times 10^4$/ml) were cultured for 48 hours in the presence of 2.5 μg/m PHA with or without $5 \times 10^3$/ml BM-MSCs or hGL-MSCs. The data are expressed as mean±SD of 4 separate experiments in triplicate. * $p<0.05$ (Student's t test). C) The clonogenic efficiency is expressed as the percentage (%) of clones obtained in each culture passage.

DETAILED DESCRIPTION OF THE INVENTION

The study conducted by the present inventors aimed at investigating whether mesenchymal stem cells are present in human adult decapsulated renal glomeruli and whether such stem cells represent a resident population. Moreover, the inventors evaluated the differentiative potential of glomeruli-derived MSCs, with particular regards to glomerular cell types such as podocytes, endothelial and mesangial cells.

Figure 1:
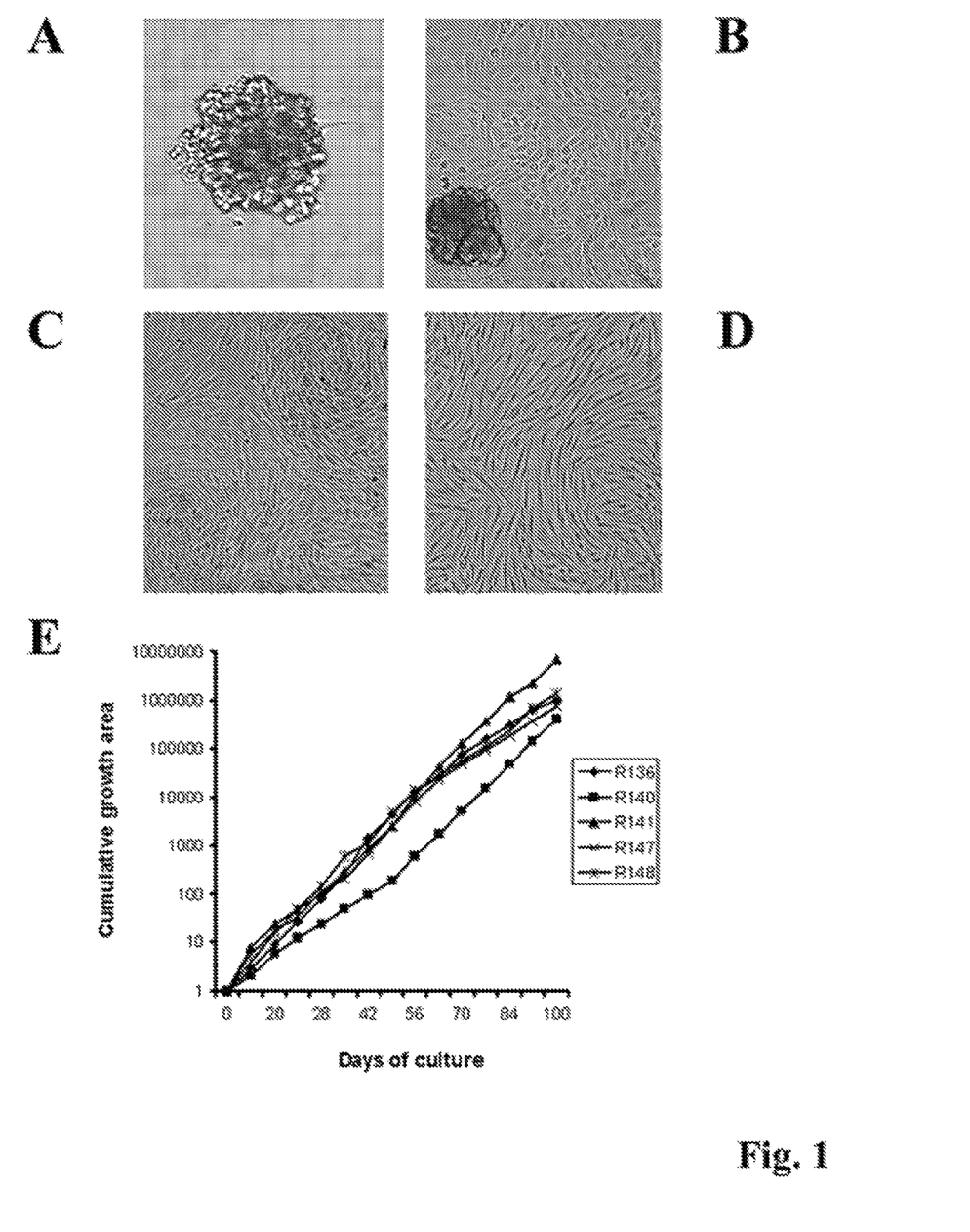
FIG. 1 shows the morphology and growth rate of cells outgrowing from glomeruli. Representative micrographs of human adult glomeruli, deprived of the Bowman's capsule by treatment with collagenase I after 24 hours (A), 7 days (B), 2 weeks (C) and 3 weeks (D) in culture (magnification ×200). E) The growth curves of 5 different preparations (designated as R136, R140, R141, R147 and R148) are shown.

As disclosed in more detail in the experimental section of the specification, the mesenchymal stem cells of the invention (hGL-MSCs) were obtained from the normal portion of the cortex from surgically removed human kidneys. After dissection of the cortex and passage through a graded series of meshes, the glomerular suspension was collected, washed and deprived of the Bowman's capsule by mechanical and enzymatic treatment. The decapsulated glomeruli (FIG. 1A) were cultured in a serum-containing buffered expansion medium under non differentiating conditions, that is to say in the absence of specific growth factors capable of directing stem cell differentiation.

Within 7 days, a glomerular outgrow of adherent cells was observed (FIG. 1B). Confluence was achieved by day 12-14 when the cell monolayer was detached by trypsin-EDTA treatment. The glomerular remnants were removed by low speed centrifugation and the cells were expanded in the same expansion medium. During the initial culture period there was a morphological heterogeneity in the cell culture (FIG. 1C) but, after about 3 weeks (i.e. about the $4^{th}$ passage), the culture became monomorphic with spindle-shaped cells (FIG. 1D). FIG. 1E shows the growth curves of 5 different cell preparations. The growth rate was slow during the five early passages, but increased with serial subculture until the $20^{th}$ passage (about 100 days of culture) when the cells were no longer capable of proliferation. The interval between passages varied between about 3 to 7 days until the $4^{th}$ passage, after which it settled at about 7 days.

The spindle-shaped cells outgrowing from decapsulated glomeruli are the human glomerular mesenchimal stem cells (hGL-MSCs) of the invention. These stem cells can therefore be isolated from the cell culture based on their morphological features, preferably from at least the $3^{rd}$ passage of cell culture or from a subsequent passage, such as for example the $4^{th}$ passage, the $5^{th}$ passage, the $6^{th}$ passage of cell culture.

The inventors further observed that the cells outgrowing from decapsulated glomeruli were a mixed population which, at the early cell passages (1-3), contain 31±11% CD133(positive) and 74±26% CD133(negative) cells (n=15 preparations), as detected by flow cytometry. Both cell populations express CD146.

Thus, as an alternative to the morphological method, the human glomerular mesenchimal stem cells (hGL-MSCs) of the invention can be isolated by a cell sorting method such as Fluorescence-Activated Cell Sorting (FACS). Preferably, the CD133(positive), CD146(positive) cells and the CD133 (negative), CD146(positive) cells are sorted by FACS from the $2^{nd}$, $3^{rd}$ or $4^{th}$ passage; however they can also be isolated from any cell passage, even before subpassaging.

The FACS-sorted populations were characterized and cloned.

CD133$^+$CD146$^+$ cells were found to co-express the markers CD31 and vWF, indicating an endothelial phenotype. This CD133$^+$ population did not co-express nestin (data not shown) nor MSC markers such as vimentin, CD73, CD29 or CD166 (data not shown). The same phenotype was observed when the CD133$^+$ cell population was immuno-magnetically sorted from the cell suspension of the digested decapsulated glomeruli (data not shown). When the cells outgrowing from renal glomeruli were characterized after the $4^{th}$ passage in the presence of the expansion medium, CD133$^+$ cells were no longer detectable.

Figure 2:
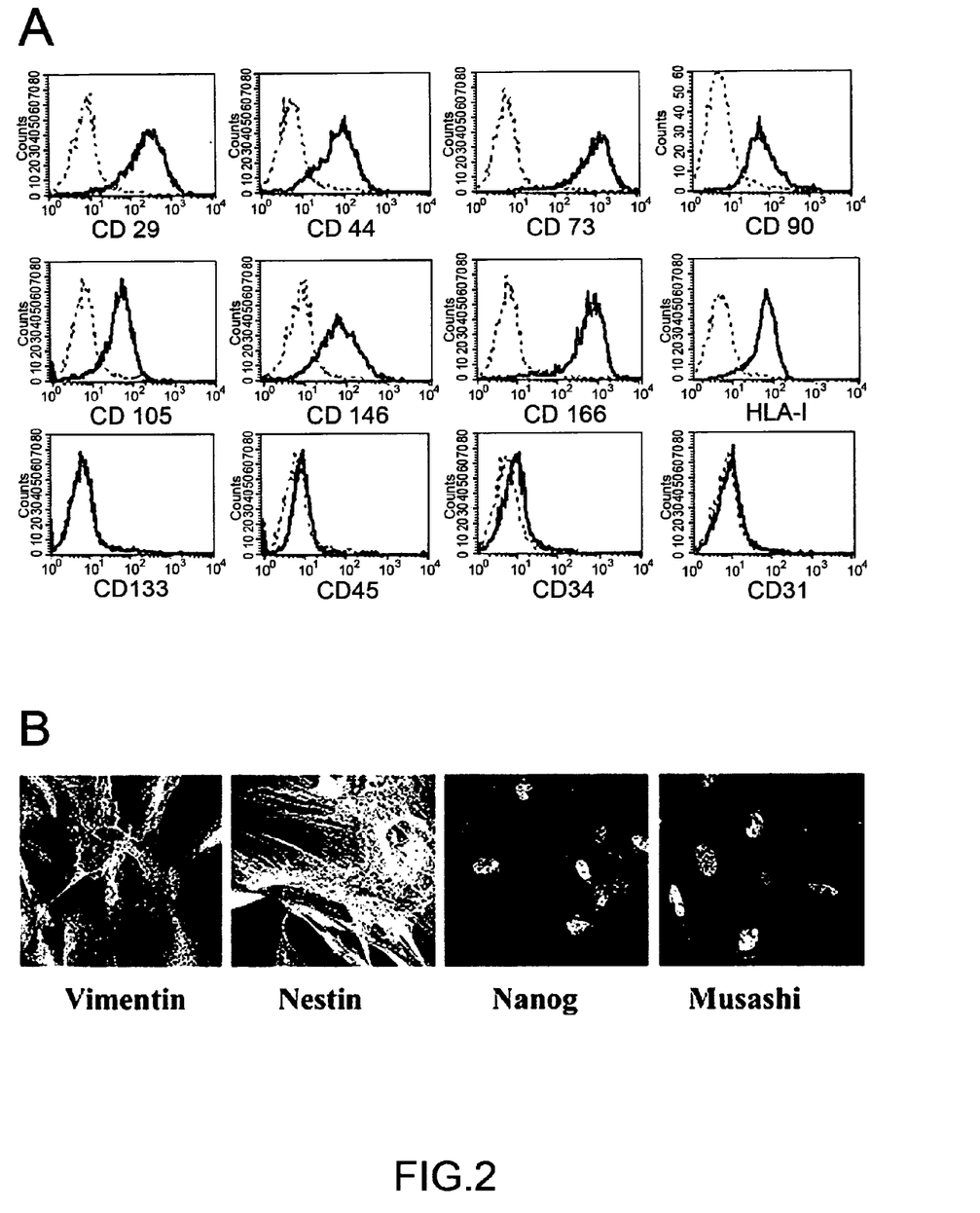
FIG. 2 relates to the characterization of the hGL-MSCs of the invention. A) Representative FACS analyses showing that the hGL-MSCs are positive for surface markers characteristic of MSCs (CD29, CD44, CD73, CD90, CD105, CD166), negative for CD133 and for specific hematopoietic markers (CD45 and CD34) and negative for endothelial markers (CD31). The dotted lines are the isotypic controls. B) Representative immunofluorescence micrographs of hGL-MSCs stained with antibodies against vimentin, nestin, Nanog and Musashi (magnification ×600). All of the developed hGL-MSC lines exhibited the same phenotype.

Sorted CD133$^-$CD146$^+$ cells were positive for surface markers characteristic of MSCs [25], including CD29, CD44, CD73, CD90, CD105 and CD166 and were negative for CD133 and specific hematopoietic markers (CD45 and CD34) as well as for endothelial markers (CD31) (FIG. 2A). By immunofluorescence, these cells expressed the MSC-specific marker vimentin and the neural and liver resident stem cell marker nestin [26, 27, 28], showing a cytoplasmic filamentous pattern (FIG. 2B). This cell population did not express the epithelial markers cytokeratin and E-cadherin. It neither expressed other markers which are usually expressed by specialized glomerular cells such as αSMA (which in contrast is expressed by mesangial cells) or nephrin (which in contrast is expresses by podocytes) (data not shown). These features indicate the absence of contaminating glomerular cells.

Figure 3:
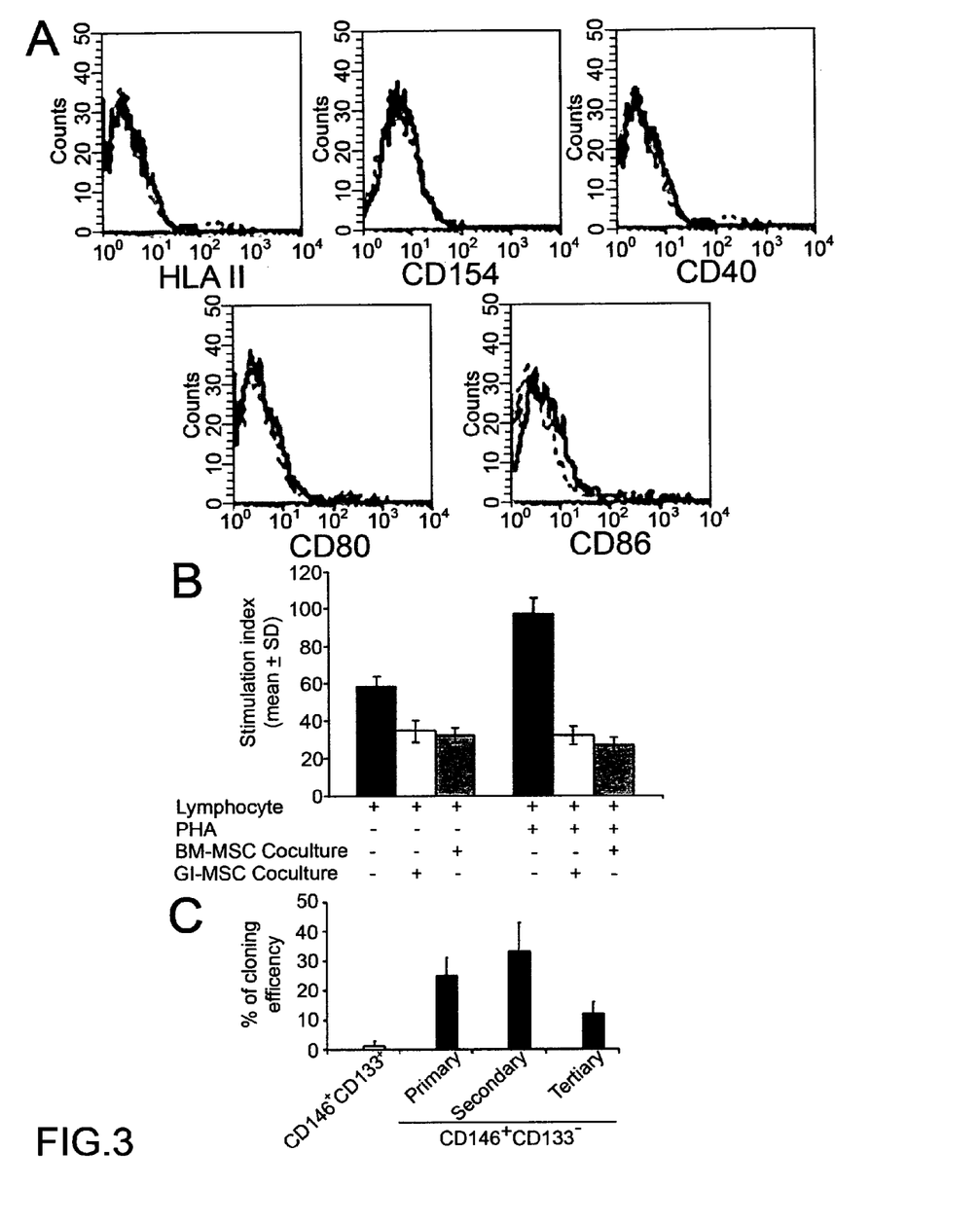

The expression of the markers Nanog, Oct-4 and Musashi was also evaluated. These molecules are transcription factors known to be involved in self-renewal and pluripotency of embryonic and adult stem cells [29-33]. The stem cell population of the invention showed nuclear-cytoplasm expression of both Nanog and Musashi (FIG. 2B), whereas it did not express Oct-4 (not shown).

hGL-MSCs were also shown to constitutively express MHC class I antigens (FIG. 2A) but they were negative for class II antigens and for the adhesion molecule CD154 and for the costimulatory molecules CD80, CD86 and CD40 (FIG. 3A), as described for BM-MSC [34]. In addition, similarly to BM-MSCs which are known to inhibit PHA-induced PBMC proliferation, hGL-MSCs induced significant reduction of PHA-induced PBMC proliferation (FIG. 3B). However, contrary to BM-MSCs, hGL-MSCs were CD24(positive) and Pax-2(positive). Furthermore, it was found that the hGL-MSCs of the invention, contrary to the renal stem cells isolated from mouse kidney, were negative for both α-SMA and Oct-4.

In order to demonstrate the self-renewal ability of the hGL-MSC populations obtained from glomeruli, the inventors carried out clonogenicity assays on the sorted CD133$^+$CD146$^+$ and CD133$^-$CD146$^+$ cells. Single-cell suspensions were seeded in 96-well plates and the outgrowing from the glomeruli at the $3^{rd}$ passage of culture in the expansion medium were sorted. The clonogenic efficiency of CD133$^-$CD146$^+$ cells was 25.3±5.1%, whereas the CD133$^+$CD146$^+$ cells were not clonogenic (FIG. 3C). Seeding of single-cell suspensions that were generated from primary clones of CD133$^-$CD146$^+$ cells provided secondary clones, and seeding of single cells that were generated from secondary clones led to the generation of tertiary clones (FIG. 3C). These data indicate that glomerular CD133$^-$CD146$^+$ cells were clonogenic and exhibited self-renewal abilities in vitro, whereas CD133$^+$CD146$^+$ cells were unable to generate clones under these culture conditions. CD133$^-$CD146$^+$ clones were analyzed by flow cytometry and immunohistochemistry and showed the same mesenchymal phenotype as the hGL-MSCs derived from the uncloned population (data not shown). When the unsorted cells outgrowing from glomeruli were characterized after the $4^{th}$ passage in the presence of the expansion medium, they all showed a mesenchymal phenotype, indicating that the culture conditions employed were selective for the expansion of hGL-MSCs.

The inventors also carried out experiments aimed at investigating whether the GL-MSCs of the invention are a resident renal population rather than a BM-derived MSC population localized within the glomeruli. For this purpose, the presence of markers differentially expressed by resident and BM-derived stem cells was first tested. hGL-MSCs expressed CD24, which in contrast is negative in the BM-derived MSCs and is considered as a marker of renal resident stem cells [2, 35]. The renal origin of hGL-MSCs was also suggested by the expression of the organ-specific embryonic Pax-2 protein and gene. Pax-2 was not expressed by BM-MSCs. Pax-2 is a transcription factor that is expressed by the stem cells of the metanephric mesenchyme [36] and by the stem cells isolated from adult rat and human kidney [1, 5]. Moreover, the inventors isolated hGL-MSCs from glomeruli of an explanted kidney from a male donor transplanted into a female recipient. hGL-MSCs derived from the transplanted kidney exhibited the same phenotype as the hGL-MSCs derived from normal kidney (data not shown). In order to assess whether the hGL-MSCs derived from the recipient's bone marrow or from the transplanted kidney, the presence of the Y chromosome in hGL-MSCs was analyzed at the $2^{nd}$ and $6^{th}$ passages. 914 nuclei and 48 metaphases were analyzed in total at the $2^{nd}$ passage (478 nuclei; 23 metaphases) plus the $6^{th}$ passage (436 nuclei; 25 metaphases). FISH analysis of the hybridisation pattern of the dual color X(green)/Y(red) centromeric probes showed that 90% of the nuclei had a male red/green pattern and 10% of the nuclei had only one green spot. The nuclei with one green spot are likely to derive from male nuclei that had lost the Y chromosome, an event that frequently occurs in culture. No female nuclei were observed (two green spots). The karyotype detected in all 48 metaphases of hGL-MSCs was male. The metaphase chromosomes, observed with DAPI used for FISH counterstaining, appeared normal. These data suggest that hGL-MSCs did not originate from the bone marrow of the recipient. Rather, they represent a resident population in the glomeruli of the donor kidney.

Since one of the most prominent features of mesenchymal stem cells is their ability to differentiate into multiple mesenchymal lineages, the inventors assessed the ability of the hGL-MSCs of the invention to differentiate into specific connective tissue cells. The CD133$^+$CD146$^+$ population sorted at the $2^{nd}$ or $3^{rd}$ passage was shown to be unable to differentiate into adipogenic, osteogenic and chondrogenic lineages under defined culture conditions (data not shown). In contrast, both the original CD133$^-$CD146$^+$ hGL-MSC lines obtained from 15 patients (at passages 4-10) and the 4 clones subsequently obtained were shown to possess multilineage differentiation abilities.

hGL-MSCs efficiently underwent osteogenic differentiation after 14 days in osteogenic medium as shown by the Alizarin Red staining of calcium deposits.

When cultured for 21 days in adipocyte-medium, hGL-MSCs generated cells containing lipidic droplets. In undifferentiated controls no evidence of mineralization or lipidic droplets was observed.

Differentiation of hGL-MSC into chondrocytes was obtained using chondrocyte-selective medium [7]. Differentiated pellets harvested at 28 days of treatment stained with Safranin O and Alcian blue, which is typical of chondrocytic differentiation [7].

Taken as a whole, these results show the multilineage differentiation abilities of the hGL-MSCs of the invention. It is also worth noticing that very similar results were obtained with the 15 hGL-MSC lines originally isolated and with the 4 clones subsequently obtained from the original cell lines The ability of hGL-MSCs to differentiate, under appropriate culture conditions, into specific glomerular cell populations, such as endothelial cells, podocytes and mesangial cells, was also evaluated. In order to obtain endothelial differentiation, hGL-MSCs were cultured for 3 weeks in EBM in the presence of VEGF. Flow cytometric analysis showed the expression of specific endothelial markers, such as CD105, KDR, CD34 and CD31. In addition, when cultured in Matrigel, endothelial differentiated hGL-MSCs and non-undifferentiated cells formed the characteristic capillary-like organization (data not shown). In the presence of PDGFbb and TGFIβ1, hGL-MSCs acquired a mesangial-like phenotype. Specifically, they acquired the expression of α-SMA and angiotensin 2 receptor 1 (AT1). When cultured for 3 weeks in the presence of 20 μM/L ATRA, hGL-MSCs acquired the expression of specific epithelial markers expressed by podocytes such as cytokeratin, podocin, nephrin and synaptopodin. Nephrin expression was confirmed by Real Time PCR, showing that the nephrin transcript was present in hGL-MSCs after differentiation into podocytes but not in hGL-MSCs maintained in the expansion medium which prevents differentiation. Three cloned cell lines were tested with similar results.

In all of the experimental conditions the differentiated cells lost the stemness related markers, such as Nanog, Musashi, vimentin, nestin, CD90, CD146, CD73, with the exception of mesangial and endothelial differentiated cells, that maintained CD90 and CD146 (data not shown), which are typically expressed by mature cells. All of the hGL-MSC cell lines and clones showed the same differentiating abilities. BM-derived MSCs under the same culture conditions were capable of differentiating into endothelial cells and muscle-like cells but not into podocyte-like cells (data not shown).

In conclusion, the inventors investigated the presence of stem cells within human glomeruli which were previously decapsulated in order to avoid the presence of stem cells associated to the Bowman's capsule. The cells outgrowing from the decapsulated glomeruli at the early passages were found to consist of two different populations: a CD133$^+$CD146$^+$ population and a CD133$^-$CD146$^+$ population. The CD133$^+$ cells most likely represent an endothelial committed cell population, since they co-express endothelial markers. Moreover, CD133$^+$CD146$^+$ cells did not survive after the $3^{rd}$ passage. In addition, when the CD133$^+$CD146$^+$ population was sorted, it was not capable of self renewal and it was not clonogenic.

In contrast, the CD133$^-$CD146$^+$ population which was isolated and cloned from decapsulated human glomeruli was found to be a multipotent population of mesenchymal stem cells capable of generating long term cultures. Interestingly, they were the only cells outgrown from glomeruli capable of surviving after the $4^{th}$ cell culture passage. These cells were designated as hGL-MSCs. hGL-MSCs shared with BM-derived MSCs and with MSCs derived from other adult tissues [9-16, 26-28] the following features: expression of CD29, CD44, CD166, CD73, CD90, CD105, CD146, vimentin and nestin; lack of CD34 and CD45; the ability to undergo mesodermal differentiation (osteocytes, chondrocytes and adipocytes). In addition, the hGL-MSCs expressed the Nanog and Musashi embryonic markers involved in cell maintenance. Like BM-derived MSCs, hGL-MSCs were capable of inhibiting the PHA-induced proliferation of PBMCs. A similar immunomodulatory effect was shown for non tubular Sca-1+lin− multipotent stem/progenitor cells from adult mice [40] and for human MSCs derived from heart, spleen and perirenal fat [41].

The origin of MSCs within adult organs has been debated. In the present study, the inventors found that the isolated hGL-MSCs possess the phenotypic characteristics of resident renal stem cells. In fact, hGL-MSCs, contrary to BM-MSCs, expressed CD24 which is considered as a marker of renal resident progenitors [2, 35], as well as the Pax-2 embryonic organ specific transcription factor [1, 5, 36]. The expression of Pax-2 has been previously shown to be a marker of renal resident stem cell populations [1, 5, 36]. Moreover, the presence of hGL-MSCs of donor sex identity in a renal allograft provided evidence for the presence of a MSC population that resides locally within the adult human glomeruli. This result is in agreement with previous evidence for tissue resident MSCs provided in human lung from studies of lung transplantation [16].

The renal commitment of hGL-MSCs is shown by their ability to differentiate into endothelial cells and into specific glomerular lineages such as podocyte and mesangial-like cells under appropriate culture conditions. Indeed, hGL-MSCs, when cultured in the presence of ATRA and type IV collagen, were able to differentiate into epithelial cells expressing markers specific for the slit diaphragm of podocytes such us nephrin, synaptopodin and podocin. This is contrast with BM-MSCs.

The differentiation of hGL-MSCs into glomerular mesangial cells was obtained by culturing the cells in the presence of a combination of TGF beta 1 and PDGF-bb, which has been reported to induce smooth muscle cell differentiation in multipotent adult progenitor cells derived from BM [20]. Moreover, hGL-MSCs showed immunomodulatory properties since they inhibited proliferation of PHA-stimulated PBMCs, similarly to BM-MSCs [23-25]. The immunomodulatory activity of hGL-MSCs is relevant for inflammatory glomerular diseases.

In conclusion, the results of the present study demonstrate the presence in adult human decapsulated glomeruli of a population of resident multipotent stem cells expressing a mesenchymal phenotype with the potential to contribute to the turn over of the different glomerular specific cell types.

The isolation of the human glomerular mesenchymal stem cells of the invention from adult human renal glomeruli and their characterising features are described in more detail in the experimental section below, which is provided by way of illustration only and is not intended to limit the scope of the invention as defined in the appended claims.

EXPERIMENTAL SECTION

Materials and Methods
Isolation and Culture of Mesenchymal Stem Cells Derived from Human Glomeruli and Bone Marrow Human mesenchymal stem cells from glomeruli (hGL-MSCs) were obtained from the normal portion of cortex from surgically removed kidneys (15 different preparations). After dissection of the cortex and passage through a graded series of meshes (60 and 120 meshes), the glomerular suspension was collected, washed with Hans Balanced Salt Solution (GIBCO, Grand Island, N.Y.) and deprived of the Bowman's capsule mechanically, by several rounds of aspiration/expulsion using a 10 ml pipette, and enzymatically, by digestion for 2 minutes with Collagenase I (Sigma, St. Louis, Mo.). Decapsulated glomeruli were transferred to fibronectin coated T25 flasks (Falcon, BD Bioscience, Two Oak Park, Bedford, Mass.).

Several culture media were compared. RPMI (Sigma) with 10% FCS (Euroclone, Wetherby, UK), in the presence of 1×ITS (Sigma) and Hepes (free acid, 10 mM) (Sigma) (expansion medium) allowed the best amplification of hGl-MSCs and therefore was used in subsequent experiments.

Human MSC were isolated from BM and cultured as previously described [7].

Growth Kinetics

Growth curves describing culture kinetics were generated as previously described [6]. The growth area occupied by a primary hGl-MSC culture, corresponding to 25 cm$^2$, was assumed as 1 as a matter of simplification. When the second passage took place, the split ratio at passage 1 (1:3) was multiplied by that value, meaning that at the end of passage 1 the cumulative growth area was 3 (i.e. three times the growth are occupied by a primary culture). At the end of the second passage, the split ratio at passage 2 (1:3) was multiplied by the cumulative growth area at passage 1 (3×3=9). This procedure was repeated for each passage, providing a theoretical growth curve that is directly proportional to the cell number. Growth was evaluated in 5 different glomerular preparations.

Characterization of Glomerular-Derived Mesenchymal Stem Cells

Cytofluorimetric analysis was performed as described [1] and the following antibodies, all phycoerythrin (PE) or fluorescein isothiocyanate (FITC) conjugated, were used: anti-CD105, -CD29, -CD31, -CD146, -CD44, -CD24, -CD90 (Dakocytomation, Copenhagen, Denmark); -CD73, -CD34, -CD45, -CD80, -CD86, -CD166, HLA-I (Becton Dickinson Biosciences Pharmingen, San Jose, Calif.); -CD133 (Miltenyi Biotec, Auburn); KDR (R&D Systems, Abington, U.K.); -HLA-II (Chemicon International Temecula, Calif.), -CD40 (Immunotech, Beckman Coulter), -CD154 (Serotec, Raleigh, N.C. USA) monoclonal antibodies. Mouse IgG isotypic controls were from Dakocytomation. All incubations were performed in 100 µl of phosphate buffered saline (PBS) containing 0.1% bovine serum albumin and 0.1% sodium azide, at 4° C. For each sample, 10,000 cells were analysed on FACSCalibur cytometer (BD Biosciences Pharmingen). Gating was constructed based on negative controls and compensation controls were included in all analyses performed. Population percentages and numbers were generated for gated populations from each experiment using Cell Quest software (BD Biosciences Pharmingen).

Indirect immunofluorescence was performed on hGL-MSCs, undifferentiated or differentiated, cultured on chamber slides (Nalgen Nunc International, Rochester, N.Y., USA), fixed in 4% paraformaldehyde containing 2% sucrose and when needed, permeabilized with Hepes-Triton ×100 buffer (Sigma). The following monoclonal antibodies were used: anti-vimentin (Sigma), anti-cytokeratin (Biomeda, Foster City Calif.), anti-E-Cadherin (Dakocytomation), alpha-smooth muscle actin (αSMA) (Dakocytomation), anti-synaptopodin (Progen Biotechnik, Heidelberg). Anti-von Willebrand factor (vWF) (Dakocytomation), anti-Nestin (Chemicon International), anti-Pax-2 (Covance, Princeton, N.J.), anti-Nanog, anti-Oct-4, anti-Musashi (AbCam, Cambridge, Science Park Cambridge UK), anti-podocin, anti-Angiotensin II Receptor 1 (AT1) (Santa Cruz Biotechnology, Santa Cruz, Calif.) rabbit polyclonal antibodies and pig polyclonal anti-Nephrin (Progen Biotechnik) were used. Omission of the primary antibodies or substitution with non immune rabbit, rat or mouse IgG were used as controls where appropriated. Alexa Fluor 488 anti-rabbit or anti-pig IgG and Texas Red anti-mouse IgG (Molecular Probes, Leiden, The Netherlands) were used as secondary Abs. Confocal microscopy analysis was performed using a Zeiss LSM 5 Pascal Model Confocal Microscope (Carl Zeiss International, Germany). Hoechst 33258 dye (Sigma) were added for nuclear staining.

Summary of Marker Expression Profile

Table 1 below provides a summary of the marker expression profile of the human glomerular mesenchymal stem cell (hGL-MSC) of the invention.

TABLE 1

| Marker | hGL-MSC |
| --- | --- |
| CD133 | Negative |
| CD146 | 100% |
| CD90 | 100% |
| CD44 | 100% |
| CD29 | 100% |
| CD73 | 100% |
| CD105 | 100% |
| CD106 | — |
| CD166 | 100% |

TABLE 1-continued

| Marker | hGL-MSC |
|---|---|
| CD45 | Negative |
| CD34 | Negative |
| CD31 | Negative |
| CD24 | 100% |
| SCA-1 | — |
| Alfa-SMA | Negative |
| Vimentin | 100% |
| Cytokeratin | Negative |
| Nestin | 100% |
| Nanog | 100% |
| Musashi | 100% |
| Oct-4 | Negative |
| Pax-2 | 100% |
| MHC-1 | 100% |
| MHC-2 | Negative |
| CD80 | Negative |
| CD86 | Negative |
| CD40 | Negative |

Fish Studies hGL-MSCs were isolated from glomeruli of an explanted kidney from a male donor transplanted into a female recipient. The patient, a female of 45 years, was transplanted with a male graft. The graft was explanted after nine mounts due to recurrence of severe nephritic syndrome resistant to therapy with a bioptic diagnosis of focal glomerulosclerosis.

The cultures at sub-confluence (70%) underwent an overnight incubation period (16-18 h) with Velbe, 0.01 μg/ml final concentration. The cells were pelleted and the pellet resuspended in hypotonic solution (0.2 g KCl+0.2 g Na citrate/100 ml). After an incubation at 37° C. for 20 min, the cells were fixed in 3:1 methanol—acetic acid and stored for 18 h at—20° C. The metaphase chromosome were prepared by dropping about 50 μl of suspension into clean glass slides and allowed to air dry before visualisation using contrast microscopy.

FISH studies were performed using commercial X (green) and Y (red) chromosome centromeric probes and Y classical satellite III heterochromatic probe (Aquarius Cytocell, Cambridge, UK). Probes were prepared and denatured according to the manufacturer's direction. Prepared probes were applied on slide containing denatured metaphases and nuclei (1.45 min in 70% formamide/2×SSC at 70° C.) under a coverslip. Hybridisation was performed overnight at 37° C. Then slides were washed once in 0.4×SSC at 72° C. for 2 min followed by a second wash of 4×SSC+Tween 20 (Sigma) at room temperature for 5-10 min. Chromosomes and nuclei were counterstained with DAPI and mounted in anti-fade solution. Samples were analyzed for the identification of male (XY)/female (XX) nuclei and metaphases with a direct microscopic visualization (Nikon epifluorescent microscope). Digital images were obtained using the Cytovision Cytogenetics Image Analysis System.

Immunomagnetically Separation, Cell Sorting and Cell Cloning

Cells were immunomagnetically separated from fresh decapsulated glomeruli or from cell cultures at the second or third passage. After dissection and passage through a graded series of meshes, suspension of decapsulated glomeruli was digested for 8 minutes with Collagenase I (Sigma) and CD133+ cells were isolated by magnetic cell sorting, using the MACS system (Miltenyi Biotech).

CD133+CD146+ and CD133−CD146+ cells from the population outgrown from the glomeruli at second and third passages of culture in the expansion medium, were separated by cell sorting (MoFlo™, Dakocytomation) and both populations were characterized, cultured and cloned by seeding of a single-cells suspension in 96-well plates by cell-sorting. The number, morphology and kinetics of resulting clones were analyzed, and some of them were selected for subcloning and differentiation assays.

In Vitro Differentiation

The adipogenic, osteogenic and chondrogenic differentiation abilities of hGL-MSCs were determined as previously described [7].

Briefly, hGL-MSCs were cultured with Adipogenic medium (Lonza, Basel Switzerland) for 3 weeks. To evaluate the differentiation, cells were fixed with 4% paraformaldehyde for 20 minutes at room temperature and stained with 0.5% Oil Red O (Sigma) in methanol (Sigma) for 20 minutes at room temperature.

Osteogenic differentiation was assessed by culturing hGL-MSCs in Osteogenic medium (Lonza). The medium was changed twice a week for 3 weeks. To evaluate the differentiation, cells were fixed with 4% paraformaldehyde for 20 minutes and stained with Alizarin Red, pH 4.1 (Lonza) for 20 minutes at room temperature.

For chondrogenic differentiation, $2.5 \times 10^5$ hGL-MSCs were centrifuged in 15-ml conical polypropylene tube (Falcon BD Bioscience) at 150 g for 5 minutes and washed twice with DMEM. The pellets were cultured in Chondrogenic medium (Lonza) supplemented with 10 ng/ml of Transforming Growth Factor β3 (Lonza). Medium were changed every 3 days for 28 days. Pellets were fixed in 4% paraformaldehyde overnight, and the paraffin-embedded sections were stained for glycosaminoglycans using 0.1% safranin O (Sigma) and for sulfated proteoglycans with 1% alcian blue.

Endothelial cell differentiation was obtained by culturing hGL-MSCs in the presence of Endothelial Basal Medium (EBM) (Lonza) with Vascular Endothelial growth factor (VEGF, 10 ng/ml, Sigma) for 3 weeks, as previously described [17].

Podocyte differentiation was obtained by culturing hGL-MSCs for 3 weeks, in the expansion medium plus all-trans retinoic acid (ATRA, Sigma, 20 μmol/L) [18]. The differentiations were performed in the chamber slides coated with type IV collagene [19] (Sigma).

Mesangial differentiation was obtained by culturing hGL-MSCs for 6 days, in DMEM High Glucose, in the presence of 10% FCS, TGF-beta 1 (2.5 ng/ml, Sigma) [20] and PDGFbb (5 ng/ml Sigma) [21]. The differentiations were performed in the chamber slides coated with fibronectin.

Real-Time PCR

Quantitative reverse-transcription PCR was performed as described previously [22]. First-strand cDNA was produced from total RNA using High Capacity cDNA Reverse Transcription Kit (Applied Biosystems, Foster City, Calif. 94404, USA). Briefly, 1 or 2 μg of mRNA, 2 μl of RT buffer, 0.8 μl of dNTP mixture, 2 μl of RT random primers, 1 μl of MultiScribe reverse transcriptase and 4.2 μl of nuclease-free water were used for each cDNA synthesis. After the reverse transcription, cDNA was stored at −20° C. Relative quantization by real-time PCR was performed using SYBR-green detection of PCR products in real-time using a 48-wells StepOne™ Real Time System (Applied Biosystems). In order to perform the real time PCR, the following sequence-specific oligonucleotide primers were used, all purchased from MWG-Biotech AG, Ebersberg, Germany: (i) the human nephrin forward and reverse primers disclosed in [22]; (ii) the human PAX2 forward and reverse primers disclosed in [1]; and (iii) the human β-actin forward and reverse primers disclosed in [1]. Power SYBR® Green PCR Master Mix was purchased from Applied Biosystems. Thermal cycling conditions were as follows: Activation of AmpliTaq Gold® DNA Polymerase LD at 95° C. for 10 min, followed by 45 cycles of amplification at 95° C. for 15 s and 60° C. (for nephrin, pax2 and for β-actin) for 1 min. To detect the log phase of amplification, the fluorescence level (quantification of product) was determined at each cycle. The cycle at which the fluorescence reached threshold was recorded, averaged between triplicates, and normalized to the averaged cycle of threshold value for β-actin. Fold change in expression with respect to control was calculated for all samples.

Allogenic Peripheral Blood Mononuclear Cells-MSC Co-Cultures

In modified mixed cell cultures, peripheral blood mononuclear cells (BPMC) from healthy volunteers were fractionated on Histopaque-1077 (Sigma) and used as responder cells and allogenic MSC were used as stimulator cells, as described [23, 24]. Briefly, hGL-MSCs were plated in triplicate onto 96-well plates at $5\times10^3$ cells/ml in 100 μl of complete media and were allowed to adhere to the plastic for 1 to 2 hours. PBMC were resuspended at $5\times10^4$ cells/ml and were added to wells (100 μl of volume) containing or not Gl-MSC, in the presence or absence of the mitogen Phytohaemagglutinin (PHA, Sigma) at the final concentration of 2.5 μg/ml. The Gl-MSC to PBMC ratio was 1:10. Human MSC form BM were used as control. The culture was maintained for 16-48 hours, after this period of culture lymphocyte proliferation was evaluated.

Cell proliferation was studied by DNA synthesis, that was detected as incorporation of 5-bromo-2'-deoxyuridine (BrdU) into the cellular DNA using an enzyme-linked immunosorbent assay kit (Chemicon International) according to the manufacturer's instructions. The data are presented as stimulation index (SI) values calculated as described [23]. The experiments were performed at least 3 times for each point described.

Statistical Analysis

Data were presented as the mean±the standard deviation from 3 or more experiments. The statistical significance was assessed by 2-tailed Student's t test.

In Vivo Localization Studies

Figure 4:
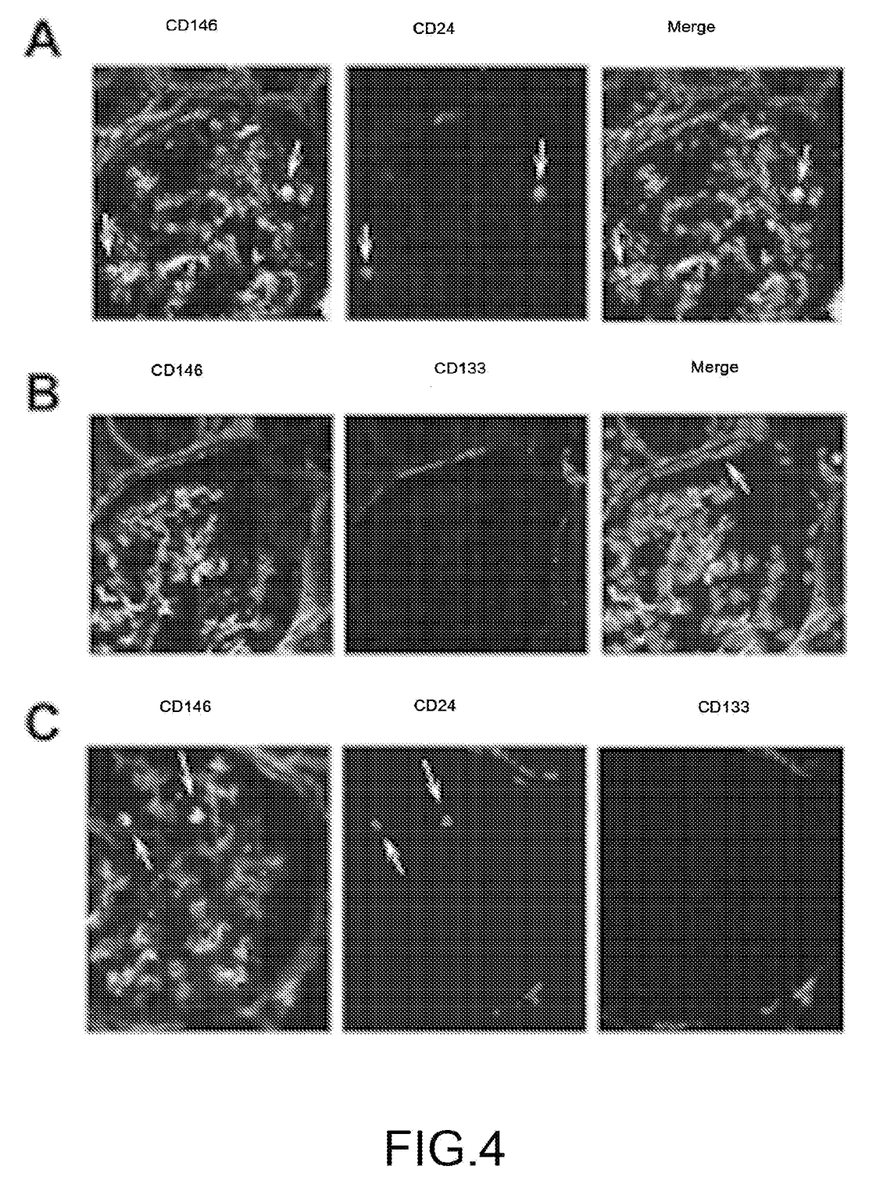
FIG. 4 is a representative confocal micrograph showing: A) co-expression of CD146 and CD24 in a glomerolus (arrows); B) expression of CD133 within the parietal cells of Bowman's capsule (arrow) and in the epithelial cells of a proximal tubule (*); and (C) absence of CD133 expression in glomerular CD146 (positive) and CD24 (positive) cells (arrows). Original 630× magnification.

The inventors also carried out experiments to define the localization in vivo, in human kidney, of the stem cell population of the invention. The results are shown in FIG. 4. The presence of CD146 (positive) and CD133 (negative) cells, co-expressing CD24 (positive) in glomeruli, was investigated by immunofluorescence. As shown in FIG. 4, CD146 (positive) cells co-expressing CD24 (positive) were detectable in glomeruli (mean 2.22±0.2/glomerulus n=60) and these cells were CD133 negative. Moreover, CD146 was expressed within the glomerular tuft by endothelial cells; CD133 (positive) cells were mainly observed in the Bowman's capsule.

REFERENCES

1. Bussolati B, Bruno S, Grange C, Buttiglieri S, Deregibus M C, Cantino D, Camussi G. Isolation of renal progenitor cells from adult human kidney. Am J Pathol. 2005; 166: 545-5.
2. Sagrinati C, Netti G S, Mazzinghi B, Lazzeri E, Liotta F, Frosali F, Ronconi E, Meini C, Gacci M, Squecco R, Carini M, Gesualdo L, Francini F, Maggi E, Annunziato F, Lasagni L, Serio M, Romagnani S, Romagnani P. Isolation and characterization of multipotent progenitor cells from the Bowman's capsule of adult human kidneys. J Am Soc Nephrol. 2006; 17: 2443-56.
3. Oliver J A, Maarouf O, Cheema F H, Martens T P, Al-Awqati Q. The renal papilla is a niche for adult kidney stem cells. J Clin Invest. 2004; 114: 795-804.
4. Maeshima A, Yamashita S, Nojima Y. Identification of renal progenitor-like tubular cells that participate in the regeneration processes of the kidney. J Am Soc Nephrol. 2003; 14: 3138-46.
5. Gupta S, Verfaillie C, Chmielewski D, Kren S, Eidman K, Connaire J, Heremans Y, Lund T, Blackstad M, Jiang Y, Luttun A, Rosenberg M E. Isolation and characterization of kidney-derived stem cells. J Am Soc Nephrol. 2006; 17:3028-40.
6. da Silva Meirelles L, Chagastelles P C, Nardi N B. Mesenchymal stem cells reside in virtually all post-natal organs and tissues. J Cell Sci. 2006; 119:2204-13.
7. Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. Science 1999; 284: 143-7.
8. Prockop D J. Marrow stromal cells as stem cells for nonhematopoietic tissues. Science. 1997; 276: 71-4.
9. Zvaifler N J, Marinova-Mutafchieva L, Adams G, Edwards C J, Moss J, Burger J A, Maini R N. Mesenchymal precursor cells in the blood of normal individuals. Arthritis Res. 2000; 2: 477-88.
10. De Bari C, Dell'Accio F, Tylzanowski P, Luyten F P. Multipotent mesenchymal stem cells from adult human synovial membrane. Arthritis Rheum. 2001; 44: 1928-42.
11. Zuk P A, Zhu M, Mizuno H, Huang J, Futrell J W, Katz A J, Benhaim P, Lorenz H P, Hedrick M H. Multilineage cells from human adipose tissue: implications for cell-based therapies. Tissue Eng. 2001; 7: 211-28.
12. Nöth U, Osyczka A M, Tuli R, Hickok N J, Danielson K G, Tuan R S. Multilineage mesenchymal differentiation potential of human trabecular bone-derived cells. J. Orthop. Res. 2002; 20: 1060-9.
13. Gronthos S, Mankani M, Brahim J, Robey P G, Shi S. Postnatal human dental pulp stem cells (DPSCs) in vitro and in vivo. Proc Natl Acad Sci USA. 2000; 97: 13625-30.
14. Young H E, Steele T A, Bray R A, Hudson J, Floyd J A, Hawkins K, Thomas K, Austin T, Edwards C, Cuzzourt J, Duenzl M, Lucas P A, Black A C Jr. Human reserve pluripotent mesenchymal stem cells are present in the connective tissues of skeletal muscle and dermis derived from fetal, adult, and geriatric donors. Anat Rec. 2001; 264: 51-62.
15. Sabatini F, Petecchia L, Tavian M, Jodon de Villeroché V, Rossi G A, Brouty-Boyé D. Human bronchial fibroblasts exhibit a mesenchymal stem cell phenotype and multilineage differentiating potentialities. Lab Invest. 2005; 85: 962-71.
16. Lama V N, Smith L, Badri L, Flint A, Andrei A C, Murray S, Wang Z, Liao H, Toews G B, Krebsbach P H, Peters-Golden M, Pinsky D J, Martinez F J, Thannickal V J. Evidence for tissue-resident mesenchymal stem cells in human adult lung from studies of transplanted allografts. J Clin Invest. 2007; 117: 989-96.
Rafii S, Lyden D, Benezra R. Vascular and haematopoietic stem cells: novel targets for anti-angiogenesis therapy? Nat Rev Cancer 2002; 2: 826-35.
17. Vaughan M R, Pippin J W, Griffin S V, Kroffi R, Fleet M, Haseley L, Shankland S J. ATRA induces podocyte differentiation and alters nephrin and podocin expression in vitro and in vivo. Kidney Int. 2005; 68: 133-44.

18. Perry J, Tam S, Zheng K, Sado Y, Dobson H, Jefferson B, Jacobs R, Thorner P S. Type IV collagen induces podocytic features in bone marrow stromal stem cells in vitro. J Am Soc Nephrol. 2006; 17: 66-76.
19. Ross J J, Hong Z, Willenbring B, Zeng L, Isenberg B, Lee E H, Reyes M, Keirstead S A, Weir E K, Tranquillo R T, Verfaillie C M. Cytokine-induced differentiation of multipotent adult progenitor cells into functional smooth muscle cells. J Clin Invest. 2006; 16: 3139-49.
20. Suzuki A, Iwatani H, Ito T, Imai E, Okabe M, Nakamura H, Isaka Y, Yamato M, Hori M. M. Platelet-derived growth factor plays a critical role to convert bone marrow cells into glomerular mesangial-like cells. Kidney Int. 2004; 65: 15-24.
21. Collino F, Bussolati B, Gerbaudo E, Marozio L, Pelissetto S, Benedetto C, Camussi G. Pre-eclamptic sera induce nephrin shedding from podocytes through endothelin-1 release by endothelial glomerular cells. Am J Physiol Renal Physiol. 2008 Feb. 20; [Epub ahead of print]
22. Di Nicola M, Carlo-Stella C, Magni M, Milanesi M, Longoni P D, Matteucci P, Grisanti S, Gianni A M. Human bone marrow stromal cells suppress T-lymphocyte proliferation induced by cellular or nonspecific mitogenic stimuli. Blood. 2002; 99: 3838-43.
23. Aggarwal S, Pittenger M F. Human mesenchymal stem cells modulate allogenic immune cell response. Blood 2005; 105: 1815-22.
24. Chamberlain G, Fox J, Ashton B, Middleton J. Concise review: mesenchymal stem cells: their phenotype, differentiation capacity, immunological features, and potential for homing. Stem Cells. 2007; 25: 2739-49.
25. El-Helou V, Dupuis J, Proulx C, Drapeau J, Clement R, Gosselin H, Villeneuve L, Manganas L, Calderone A. Resident nestin+ neural-like cells and fibers are detected in normal and damaged rat myocardium. Hypertension. 2005; 46: 1219-25.
26. Mayer E J, Carter D A, Ren Y, Hughes E H, Rice C M, Halfpenny C A, Scolding N J, Dick A D. Neural progenitor cells from postmortem adult human retina. Br J Ophthalmol. 2005; 89: 102-6.
27. Herrera M B, Bruno S, Buttiglieri S, Tetta C, Gatti S, Deregibus M C, Bussolati B, Camussi G. Isolation and characterization of a stem cell population from adult human liver. Stem Cells. 2006; 24:2840-50.
28. Hatano S Y, Tada M, Kimura H, Yamaguchi S, Kono T, Nakano T, Suemori H, Nakatsuji N, Tada T. Pluripotential competence of cells associated with Nanog activity. Mech Dev. 2005; 122:67-79.
29. Cavaleri F, Scholer H R. Nanog: a new recruit to the embryonic stem cell orchestra. Cell 2003; 113: 551-2.
30. Tai M H, Chang C C, Kiupel M, Webster J D, Olson L K, Trosko J E. Oct4 expression in adult human stem cells: evidence in support of the stem cell theory of carcinogenesis. Carcinogenesis. 2005; 26: 495-502.
31. Potten C S, Booth C, Tudor G L, Booth D, Brady G, Hurley P, Ashton G, Clarke R, Sakakibara S, Okano H. Identification of a putative intestinal stem cell and early lineage marker; musashi-1. Differentiation. 2003; 71:28-41.
32. Sugiyama-Nakagiri Y, Akiyama M, Shibata S, Okano H, Shimizu H. Expression of RNA-binding protein Musashi in hair follicle development and hair cycle progression. Am J Pathol. 2006; 68: 80-92.
33. Le Blanc K, Tammik C, Rosendahl K, Zetterberg E, Ringdén O. HLA expression and immunologic properties of differentiated and undifferentiated mesenchymal stem cells. Exp Hematol. 2003; 31: 890-96.
34. Challen G A, Martinez G, Davis M J, Taylor D F, Crowe M, Teasdale R D, Grimmond S M, Little M H. Identifying the molecular phenotype of renal progenitor cells. J Am Soc Nephrol. 2004; 15: 2344-57.
35. Oliver J A, Barasch J, Yang J, Herzlinger D, Al-Awqati Q. Metanephric mesenchyme contains embryonic renal stem cells. Am J Physiol. 2002; 283: F799-F809.
36. Kitamura S, Yamasaki Y, Kinomura M, Sugaya T, Sugiyama H, Maeshima Y, Makin H. Establishment and characterization of renal progenitor like cells from S3 segment of nephron in rat adult kidney. FASEB J. 2005; 19: 1789-97.
37. Challen G A, Bertoncello I, Deane J A, Ricardo S D, Little M H. Kidney side population reveals multilineage potential and renal functional capacity but also cellular heterogeneity. J Am Soc Nephrol. 2006; 17: 1896-1912.
38. Lazzeri E, Crescioli C, Ronconi E, Mazzinghi B, Sagrinati C, Netti G S, Angelotti M L, Parente E, Ballerini L, Cosmi L, Maggi L, Gesualdo L, Rotondi M, Annunziato F, Maggi E, Lasagni L, Serio M, Romagnani S, Vannelli G B, Romagnani P. Regenerative potential of embryonic renal multipotent progenitors in acute renal failure. J Am Soc Nephrol. 2007; 18: 3128-3138.
39. Dekel B, Zangi L, Shezen E, Reich-Zeliger S, Eventov-Friedman S, Katchman H, Jacob-Hirsch J, Amariglio N, Rechavi G, Margalit R, Reisner Y. Isolation and characterization of nontubular sca-1+lin– multipotent stem/progenitor cells from adult mouse kidney. J Am Soc Nephrol. 2006; 17: 3300-3314.
40. Hoogduijn M J, Crop M J, Peeters A M, Van Osch G J, Balk A H, Ijzermans J N, Weimar W, Baan C C. Human heart, spleen, and perirenal fat-derived mesenchymal stem cells have immunomodulatory capacities. Stem Cells Dev. 2007; 16: 597-604.

The invention claimed is:

1. An isolated multipotent gliomerular mesenchymal stem cell derived from adult human kidney glomeruli (hGL-MSC) expanded in vitro over multiple passages, characterised by the markers CD133(negative), CD146(positive), CD34(negative), CD105(positive), CD24(positive), Oct-4 (negative), and Pax-2(positive) and further characterised by the ability to differentiate into at least the following cell types: podocytes, endothelial cells and mesangial cells.

2. The multipotent glomerular mesenchymal stem cell derived from adult human kidney glomeruli (hGL-MSC) according to claim 1, which is further capable of undergoing osteogenic, adipogenic and chondrogenic differentiation.

3. The multipotent glomerular mesenchymal stem cell derived from adult human kidney glomeruli (hGL-MSC) according to claim 1, which is further characterized as negative for the marker α-SMA.

4. The multipotent glomerular mesenchymal stem cell derived from adult human kidney glomeruli (hGL-MSC) according to claim 1, which is further characterized as negative for the marker CD45.

5. The multipotent glomerular mesenchymal stem cell derived from adult human kidney glomeruli (hGL-MSC) according to claim 1, which is further characterized as negative for the marker CD31.

6. The multipotent glomerular mesenchymal stem cell derived from adult human kidney glomeruli (hGL-MSC) according to claim 1, which is positive for a surface marker characteristic of mesenchymal stem cells selected from the group consisting of CD29, CD44, CD73, CD90, CD166 or any combination thereof.

7. The multipotent glomerular mesenchymal stem cell derived from adult human kidney glomeruli (hGL-MSC) according to claim 1, which is further characterized as positive for the markers Nanog and Musashi.

8. The multipotent glomerular mesenchymal stem cell derived from adult human kidney glomeruli (hGL-MSC) according to claim 1, which is further characterized as positive for vimentin and nestin and negative for cytokeratin.

9. The multipotent glomerular mesenchymal stem cell derived from adult human kidney glomeruli (hGL-MSC) according to claim 1, which constitutively expresses MHC class I antigens and is further characterized as negative for MHC class II antigens.

10. The multipotent glomerular mesenchymal stem cell derived from adult human kidney glomeruli (hGL-MSC) according to claim 9, which is further characterized as negative for the costimulatory molecules CD80, CD86 and CD40.

11. A pharmaceutical composition comprising the isolated human glomerular mesenchymal stem cell (hGL-MSC) expanded in vitro over multiple passages according to claim 1 and a pharmaceutically acceptable carrier, diluent and/or vehicle.

12. A method for treating a kidney injury or disease in a subject, comprising administering to the subject an effective amount of the isolated expanded multipotent glomerular mesenchymal stem cell derived from human kidney (hGL-MSC) according to claim 1.

13. A method according to claim 12, wherein the kidney injury or disease is a renal glomerulus injury or disease.

14. A therapeutic method of kidney regeneration in a subject in need thereof, comprising administering to the subject an effective amount of the isolated expanded multipotent glomerular mesenchymal stem cell derived from human kidney (hGL-MSC) according to claim 1.

15. A method for treating a kidney injury or disease in a subject, comprising administering to the subject an effective amount of the isolated expanded multipotent glomerular mesenchymal stem cell derived from human kidney (hGL-MSC) according to the pharmaceutical composition according to claim 11.

16. A therapeutic method of kidney regeneration in a subject in need thereof, comprising administering to the subject an effective amount of the isolated expanded multipotent glomerular mesenchymal stem cells derived from human kidney (hGL-MSC) according to the pharmaceutical composition according to claim 11.

\* \* \* \* \*